United States Patent [19]

Sikkenga et al.

[11] Patent Number: 5,118,892
[45] Date of Patent: * Jun. 2, 1992

[54] PREPARATION OF A DIMETHYLNAPHTHALENE

[75] Inventors: David L. Sikkenga; Ian C. Zaenger, both of Wheaton, Ill.; Gregory S. Williams, Tampa, Fla.

[73] Assignee: Amoco Corporation, Chicago, Ill.

[*] Notice: The portion of the term of this patent subsequent to Aug. 21, 2007 has been disclaimed.

[21] Appl. No.: 556,350

[22] Filed: Jul. 20, 1990

Related U.S. Application Data

[63] Continuation-in-part of Ser. No. 316,309, Feb. 27, 1989, Pat. No. 5,012,024, which is a continuation-in-part of Ser. No. 210,999, Jun. 24, 1988, abandoned.

[51] Int. Cl.$^5$ ............................................. C07C 15/24
[52] U.S. Cl. ................................... 585/320; 585/440; 585/441; 585/444; 585/481; 585/482
[58] Field of Search ............... 585/320, 440, 441, 444, 585/481, 482

[56] References Cited

U.S. PATENT DOCUMENTS

| 3,723,557 | 3/1973 | Hayes | 585/444 |
| 3,775,496 | 11/1973 | Thompson | 585/320 |
| 3,781,375 | 12/1973 | Shima et al. | 585/400 |
| 3,803,253 | 4/1974 | Sold et al. | 585/481 |
| 3,957,896 | 5/1976 | Yokoyama et al. | 585/481 |
| 4,950,825 | 8/1990 | Sikkenga et al. | 585/320 |
| 4,962,260 | 10/1990 | Sikkenga et al. | 585/481 |

*Primary Examiner*—Anthony McFarlane
*Assistant Examiner*—Nhat Phan
*Attorney, Agent, or Firm*—Thomas E. Nemo; William H. Magidson; Frank J. Sroka

[57] ABSTRACT

A method for preparing one or more diemthylnaphthalenes from one or more dimethyltetralins, and optionally for preparing one or more other specific dimethylnaphthalenes by isomerization of the aforesaid dimethylnaphthalene(s) is disclosed.

33 Claims, No Drawings

PREPARATION OF A DIMETHYLNAPHTHALENE

RELATED APPLICATION

This application is a continuation-in-part of pending patent application Ser. No. 316,309, filed Feb. 27, 1989, now U.S. Pat. No. 5,012,024, which is a continuation-in-part of patent application Ser. No. 210,999, filed Jun. 24, 1988, and now abandoned.

BACKGROUND OF THE INVENTION

1. Field of the Invention

This invention relates generally to a method for preparing one or more specific dimethylnaphthalene isomers by dehydrogenating one or more specific dimethyltetralin isomers.

2. Description of the Prior Art

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Dimethylnaphthalenes are desirable feedstocks for oxidation to the corresponding naphthalene dicarboxylic acids. A known conventional process for producing a naphthalene dicarboxylic acid comprises the oxidation of a dimethylnaphthalene with oxygen in the liquid phase in an acetic acid solvent at an elevated temperature and pressure and in the presence of a catalyst comprising cobalt, manganese and bromine components.

Typically dimethylnaphthalenes are found in refinery or coal-derived streams as mixtures of all of the ten possible dimethylnaphthalene isomers. However, separation of these isomers is very difficult and expensive. Consequently, methods for producing specific dimethylnaphthalenes or mixtures of two or three specific dimethylnaphthalenes in high purity and quality are highly desirable. One type of such method is a multistep synthesis involving (1) the formation of an alkenylbenzene by the reaction of o-, m- or p-xylene or ethylbenzene with butadiene, (2) the cyclization of the resulting alkenylbenzene to form one or more dimethyltetralins belonging to one or two of three groups of three isomeric dimethyltetralins —that is, either group A containing the 1,5-, 1,6-, 2,5- and 2,6-dimethyltetralins, group B containing the 1,7-, 1,8-, 2,7- and 2,8-dimethyltetralins, or group C containing the 1,3-, 1,4-, 2,3-, 5,7-, 5,8- and 6,7-dimethyltetralins—(3) the dehydrogenation of the dimethyltetralin(s) to form the corresponding dimethylnaphthalene(s), and (4) the isomerization of the resulting dimethylnaphthalene(s) to the desired specific dimethylnaphthalene.

For example, Thompson, U.S. Pat. Nos. 3,775,496; 3,775,497; 3,775,498; 3,775,500 disclose processes for the cyclization of specific alkenylbenzenes to one or more specific dimethyltetralins at 200°–450° C. in the presence of any suitable solid acidic cyclization catalyst such as acidic crystalline zeolites as well as silica-alumina, silica-magnesia and silica-alumina-zirconia and phosphoric acid, followed by the dehydrogenation of the resulting dimethyltetralin(s) in the vapor state to the corresponding dimethylnaphthalene(s) in a hydrogen atmosphere at 300°–500° C. and in the presence of a solid dehydrogenation catalyst such as noble metals on carriers and chromia-alumina, and thereafter isomerization of each of the aforesaid dimethylnaphthalene(s) to the desired isomer within the triad of dimethylnaphthalenes to which the isomer being isomerized belongs, at 275°–500° C. in the presence of a solid acidic isomerization catalyst of the same type as described in respect of the cyclization disclosed therein. In the alternative, both the cyclization and isomerization reactions can be performed in the liquid phase, in which case the cyclization is performed at 200°–275° C. with a solid phosphoric acid catalyst, at 70°–140° C. with an acidic ion exchange resin, an acidic crystalline zeolite, hydrofluoric or sulfuric acid as the catalyst or a siliceous cracking catalyst.

More specifically, Thompson, U.S. Pat. No. 3,775,496 discloses the cyclization of 5-(m-tolyl)-pent-2-ene to 1,6- and 1,8-dimethyltetralins, which are then dehydrogenated to 1,6- and 1,8-dimethylnaphthalenes, which in turn are isomerized to 2,6- and 2,7-dimethylnaphthalenes, respectively. Thompson, U.S. Pat. No. 3,775,497 discloses the cyclization of 5-phenyl-hex-2-ene to 1,4-dimethyltetralin which is then dehydrogenated to 1,4-dimethylnaphthalene, which is in turn isomerized to 2,3-dimethylnaphthalene. Thompson, U.S. Pat. No. 3,775,498 discloses the cyclization of 5-(o-tolyl)-pent-2-ene to 1,5-dimethyltetralin, which is then dehydrogenated to 1,5-dimethylnaphthalene, which is in turn isomerized to 2,6-dimethylnaphthalene. Thompson, U.S. Pat. No. 3,775,500 discloses the cyclization of 5-(p-tolyl)-pent-2-ene to 1,7-dimethyltetralin, which is then dehydrogenated to 1,7-dimethylnaphthalene, which in turn is isomerized to 2,7-dimethylnaphthalene.

Shimada et al., U.S. Pat. No. 3,780,119 disclose a method for the isomerization of dimethylnaphthalene by the use at a temperature above 260° C. of a mordenite catalyst in which a metal form of mordenite is in excess of 20 weight percent of the mordenite, with the metal being selected from the group consisting of lithium, sodium, potassium, magnesium, calcium, strontium, barium, zinc and aluminum.

Suld et al., U.S. Pat. No. 3,803,253 disclose a method for the hydroisomerization of a dimethylnaphthalene by the use of a combination of a hydrogenation catalyst and a calcium-containing zeolite catalyst, such as a calcium-exchanged synthetic faujasite, for example, a Y-type molecular sieve.

Shima et al., U.S. Pat. No. 3,806,552 disclose a method for the isomerization of dimethylnaphthalenes in the gas phase by the use of a mixed catalyst consisting of (a) 65–95 weight percent of a hydrogen form of mordenite in which above 80 weight percent of the metal cations are replaced with hydrogen ions, and (b) 5–35 weight percent of catalyst selected from the group consisting of bentonite and fuller's earth.

Hedge, U.S. Pat. No. 3,855,328 discloses a method for the isomerization of dimethylnaphthalenes by the use of a Type Y alumino silicate zeolite at 120°–300° C. in the liquid phase. The catalysts have aluminum-to-silicon atomic ratios of 0.1–1.0.

Ogasawara et al., U.S. Pat. No. 3,888,938 disclose a method for the isomerization of dimethylnaphthalenes in the liquid phase by the use of a mixed catalyst consisting of (a) 70–95 weight percent of a hydrogen form of mordenite in which above 80 weight percent of the metal cations are replaced with hydrogen ions, and (b) 5–30 weight percent of a promoter selected from the group consisting of bentonite and fuller's earth.

Hedge et al., U.S. Pat. No. 3,928,482 disclose the isomerization of either dimethyldecalins, dimethyltetralins or dimethylnaphthalenes in the presence of an alumino silicate zeolite containing polyvalent metal cations in exchange positions, such as a rare earth-exchanged Type Y zeolite.

Yokayama et al., U.S. Pat. No. 3,957,896 disclose the selective isomerization of dimethylnaphthalenes in the presence of any kind of natural or synthetic, solid acid catalyst, such as Y-type zeolite as well as silica-alumina, silica-magnesia, silica-zirconia, silica-aluminazirconia, fuller's earth, natural or synthetic mordenite, X-type zeolite, A-type zeolite and L-type zeolite. These catalysts may be substituted partly or wholly by hydrogen or metal. Furthermore, these catalysts can be unsupported or supported on carriers.

Onodera et al., U.S. Pat. No. 4,524,055 discloses a crystalline aluminosilicate zeolite that is useful in the isomerization of dimethylnaphthalenes and has a silica-to-alumina mole ratio of 10 to 100, specific x-ray lattice distances, and a specific cylohexane-to-n-hexane adsorption ratio of at least 0.7.

Maki et al., U.S. Pat. No. 4,556,751 disclose the isomerization of dimethylnaphthalenes in the presence of a crystalline aluminosilicate having a pentasil structure and a silica-to-alumina molar structure of 12 or higher. In addition, the aluminosilicate may contain some other metals as non-exchangeable metals.

A problem in all such prior art methods is the presence of other dimethylnaphthalene isomers and unconverted dimethyltetralin as impurities and by-products in the finally obtained, desired specific dimethylnaphthalene isomer. The presence of such impurities and by-products markedly reduces the utility and commercial value of the desired dimethylnaphthalene isomer, especially as a precursor for the formation of a naphthalene dicarboxylic acid for use as a monomer in the manufacture of a polymer. In addition, catalysts tend to deactivate relatively rapidly at the high temperatures employed in vapor phase processes. Therefore, it is highly desirable to employ liquid phase processes and to improve the completeness of each step in the aforesaid multistep synthesis and the selectivity of each step therein for the production of the desired product therefrom.

In this regard, it is known that in the presence of an acid catalyst, the dimethylnaphthalene isomers are isomerizable within each triad of dimethylnaphthalene isomers—that is, within the 1,5-, 1,6- and 2,6-dimethylnaphthalenes of triad A, within the 1,7-, 1,8-, and 2,7-dimethylnaphthalenes of triad B, and within the 1,3-, 1,4- and 2,3-dimethylnaphthalenes of triad C. It is also known that the interconversion of a dimethylnaphthalene isomer within one of the aforesaid triads to a dimethylnaphthalene isomer within another of the aforesaid triads occurs to a relatively lesser extent. However, it is highly desired to improve the selectivity and completeness of the aforesaid dehydrogenation and isomerization steps in the aforesaid multistep synthesis for the formation of the specific dimethylnaphthalene isomer(s) desired.

OBJECTS OF THE INVENTION

It is therefore a general object of the present invention to provide an improved method for manufacturing with an improved yield and selectivity a specific dimethylnaphthalene isomer or set of dimethylnaphthalene isomers which meets the aforementioned requirements for selectivity and completeness and catalyst activity.

It is a related object of the present invention to provide an improved method for manufacturing with an improved yield and selectivity a specific dimethylnaphthalene isomer or set of dimethylnaphthalene isomers by the dehydrogenation of a specific dimethyltetralin isomer or a set of dimethyltetralin isomers, and optionally then isomerizing the resulting first dimethylnaphthalene(s) to one or more other dimethylnaphthalene isomers that belong to the same triad or triads as do the first dimethylnaphthalene isomer(s).

Other objects and advantages of the method of the present invention will become apparent upon reading the following detailed description and appended claims.

SUMMARY OF THE INVENTION

The objects are achieved by an improved method for preparing a dimethylnaphthalene comprising: contacting a first feedstock comprising at least one dimethyltetralin in liquid form with a solid dehydrogenation catalyst in a reaction vessel at an elevated temperature and at a pressure that is sufficiently high to maintain the first feedstock substantially in the liquid phase, to thereby effect conversion of the aforesaid dimethyltetralin in an equilibrium dehydrogenation reaction to form hydrogen and a first liquid product comprising a dimethylnaphthalene formed from each aforesaid dimethyltetralin, and removing a substantial portion of the hydrogen being formed in the dehydrogenation reaction from the reaction vessel to thereby shift the aforesaid equilibrium toward the formation of the dimethylnaphthalene product.

DETAILED DESCRIPTION OF THE PREFERRED EMBODIMENTS

Any dimethyltetralin or mixture of dimethyltetralins is suitable for use as a feedstock in the method of this invention. In the method of the present invention, the dehydrogenation step is followed preferably by an isomerization step in which the dimethylnaphthalene(s) produced in the dehydrogenation step is isomerized to the desired dimethylnaphthalene(s). Thus, if a particular dimethylnaphthalene or set of dimethylnaphthalenes is desired as the final product, then it is preferred to use a dimethyltetralin or set of dimethyltetralins that form by the dehydrogenation of the method of the present invention either (1) such dimethylnaphthalene(s) directly or (2) other dimethylnaphthalene(s) which belong to the same triad or triads of dimethylnaphthalene isomers to which the desired dimethylnaphthalene isomer(s) belong, and which can then be isomerized in the preferred method of this invention to the desired dimethylnaphthalene(s).

In addition or in the alternative, the specific dimethyltetralin or set of specific dimethyltetralins employed in the dehydrogenation step of the method of this invention can depend on the manner in which each dimethyltetralin employed is obtained. For example copending U.S. patent application Ser. No. 316,308, filed Feb. 27, 1989 and Sikkenga, Lamb, Zaenger and Williams, copending U.S. patent application Ser. No. 556,297, filed concurrently herewith (the entire disclosures of which are specifically incorporated herein by reference), disclose the formation of one or more dimethyltetralins by the cyclization of 5-(o-, m-, or p-tolyl)-pent-1- or -2-ene or 5-phenyl-hex-1- or -2-ene, and thereafter the dehydrogenation of the resulting dimethyltetralin(s) to form one or more corresponding dimethylnaphthalenes.

When 5-(o-tolyl)-pent-1- or -2-ene is the feedstock to the aforesaid cyclization step, 1,5-, 1,6-, 2,5-, or 2,6-dimethyltetralin or a mixture thereof comprises at least 80, preferably at least 85 weight percent of the dimethyltetralins produced therefrom, which resulting dimethytetralins are in turn the feedstock and are converted in the dehydrogenation step of the present invention to the corresponding 1,5-, 1,6- and 2,6-dimethylnaphthalenes, which are then the feedstock in the isomerization step of the preferred embodiment of the present invention and are converted therein to 2,6-dimethylnaphthalene.

When 5-(m-tolyl)-pent-1- or -2-ene is the feedstock to the aforesaid cyclization step, 1,5- 1,6- 1,7-, 1,8- 2,5- 2,6-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step of the present invention to the corresponding 1,5-, 1,6-, 1,7-, 1,8- 2,6- and 2,7-dimethylnaphthalenes, which are then the feedstock in the isomerization step of the present invention and are converted therein to 2,6- and 2,7-dimethylnaphthalenes.

When 5-(p-tolyl)-pent-1- or -2-ene is the feedstock to the aforesaid cyclization step, 1,7-, 1,8-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step of the present invention to the corresponding 1,7-, 1,8- and 2,7-dimethylnaphthalenes which are then the feedstock and are converted in the isomerization step of the present invention to 2,7-dimethylnaphthalene.

When 5-phenyl-1- or -2-hexene is the feedstock to the aforesaid cyclization step, 1,3-, 1,4-, 2,3-, 5,7, 5,8-, or 6,7-dimethyltetralin or a mixture thereof comprises at least 80, preferably at least 85 weight percent of the dimethyltetralins produced therefrom, which dimethyltetralins are in turn the feedstock and are converted in the dehydrogentation step of the present invention to the corresponding, 1,3-, 1,4- and 2,3-dimethylnaphthalenes, which are then the feedstock in the isomerization step of the present invention and are converted to 2,3-dimethylnaphthalene therein.

In the method of the present invention, each of the aforesaid dehydrogenation reaction and optional isomerization reaction is performed in the liquid phase at an elevated temperature and at a sufficiently high pressure to ensure that the feedstock for the particular step is maintained substantially in the liquid phase. By elevated temperature it is meant a temperature sufficiently high so that a significant portion of the feedstock for the respective reaction is converted to the desired product using preselected catalyst levels and reaction times for batch processes, or preselected space velocities for continuous processes. The dehydrogenation reaction is preferably performed at a temperature in the range of about 200° C., more preferably about 220° C., to about 500° C., more preferably to about 450° C. Most preferably, the dehydrogenation reaction is performed at a temperature in the range of about 220° C. to about 420° C. Preferably, the dehydrogenation reaction is performed at a pressure in the range of about 0.1, more preferably about 1.0, to about 30.0, more preferably to about 20.0 atmospheres absolute. The isomerization reaction is preferably performed at a temperature in the range of about 200° C., more preferably about 240° C., to about 420° C., more preferably to about 380° C. Most preferably the isomerization reaction is performed at a temperature in the range of about 240° C. to about 350° C. The isomerization reaction is preferably performed at a pressure in the range of about 0.1, more preferably about 0.5, to about 20.0, more preferably 5.0 atmospheres absolute.

Each of the dehydrogenation and isomerization reactions can be performed with or without a solvent for the respective feedstock. Preferably a solvent is not employed in the aforesaid steps. If employed, a solvent in any of the aforesaid steps must be inert under the conditions employed and suitably comprises a paraffin such as a tetradecane, or an aromatic hydrocarbon such as anthracene, or mixtures thereof, which preferably boils above about 270° C.

Each of the dehydrogenation and isomerization steps of the method of the present invention can be performed either batchwise or continuously. The reaction apparatus to be used in each aforesaid step can be of any known type such as a fixed bed, moving bed, fluidized bed, liquid phase suspended bed or a solid-liquid mixture in a stirred tank. Generally, however, the use of a fixed bed is commercially preferred for continuous operation. When conducting the dehydrogenation reaction of this invention in a continuous manner, it is advantageous to use two or more fixed bed reactors in series. Hydrogen formed during the dehydrogenation reaction is preferably removed from the product mixture between such fixed bed reactors arranged in series.

The improved conversion of the feedstock and selectivity for the production of the desired product or set of products for each of the dehydrogenation and isomerization steps of the method of this invention are the result of the temperature and pressure conditions employed and the high activity and selectivity of the catalysts employed in each aforesaid step, which in turn permits the use of less severe conditions—that is, lower temperatures and pressures—such that greater selectivity and reduced catalyst deactivation can be achieved.

The catalyst employed in the dehydrogenation step of the method of this invention is any solid dehydrogenation catalyst that is capable of effecting the dehydrogenation and exhibiting a reasonable lifetime under the conditions employed, including catalysts such as noble metals on carriers such as reforming catalysts. Aluminas, silicas, alumina-silicas, and activated carbons are examples of suitable carriers or supports. The noble metals include, for example, platinum, palladium, ruthenium and rhenium. The noble metal component can also comprise mixtures of two or more noble metals. Preferably, palladium on an active carbon or alumina support containing from about 0.5, more preferably from about 1.0, to about 15, more preferably to about 10 weight percent of palladium, calculated as elemental palladium and based on the weight of the catalyst, is employed as the dehydrogenation catalyst.

Other preferred dehydrogenation catalysts include platinum on activated carbon or alumina supports, rhenium on activated carbon or alumina supports and mixtures of platinum and rhenium on activated carbon or alumina supports, wherein the platinum and rhenium are each present from about 0.01, preferably 0.05, to about 10.0, preferably 5.0 weight percent calculated as the element and based on the weight of the catalyst. A more preferred dehydrogenation catalyst comprises a mixture of platinum and rhenium on gamma alumina where the platinum and rhenium are each present in the range of about 0.1 to about 10.0 weight percent calculated as the element, and based on the weight of the catalyst. A support material such as an alumina or other non-combustible support material has an advantage over a carbon support material in that the non-combustible support can be exposed to air or other source of oxygen-containing gas at an elevated temperature to regenerate a deactivated catalyst. Consequently, such a catalyst can be cycled wherein between each cycle of use as a dehydrogenation catalyst the catalyst is regenerated with an oxygen-containing gas at an elevated temperature. Preferably the level of oxygen in the oxygen-containing gas is about 1 wt % to about 25 wt %, the regeneration temperature is in the range of about 400° C. to about 600° C. and the time of exposure to the oxygen-containing gas at these temperatures is that sufficient to regenerate the catalyst.

In the liquid phase dehydrogenation reactions of this invention, when conducted in either a batch or continuous manner, and particularly when using the preferred dehydrogenation catalysts, the addition of hydrogen to the reaction mixture is not necessary to maintain catalyst activity during extended catalyst use, i.e., the liquid phase dehydrogenation reaction in the method of this invention wherein a dimethyltetralin is dehydrogenated to a dimethylnaphthalene proceeds in the absence of hydrogen added to the reaction mixture. Without intending to be bound by a theory of operation, it appears that during the liquid phase dehydrogenation method of this invention wherein dimethyltetralins are dehydrogenated to dimethylnaphthalenes using a dehydrogenation catalyst, and particularly the preferred noble metal dehydrogenation catalysts disclosed herein, the hydrogen generated during the dehydrogenation reaction effectively maintains catalyst activity.

In the dehydrogenation method of this invention it is advantageous to remove hydrogen during the liquid phase dehydrogenation reaction. This is accomplished in a batch procedure by venting the hydrogen from the vessel used to conduct the batch reaction. If operating in a continuous mode, a plurality of series arranged fixed bed reactors can be utilized with the hydrogen vented from the process stream between fixed bed reactors. Other suitable methods for venting the hydrogen from a fixed bed reactor can be used.

If the dehydrogenation is performed on a batch basis, the catalyst is employed at a level in the range of from about 0.005, preferably from about 0.01, to about 1.0, preferably to about 0.2 weight percent of the noble metal component, calculated as the elemental noble metal and based on the weight of the dimethyltetralin feedstock, and the reaction time is from about 1, preferably from about 2, to about 50, preferably to about 40 hours. If the dehydrogenation is performed on a continuous basis, the space velocity is in the range of from about 0.1, preferably from about 10, to about 5000, preferably to about 2000 parts of the dimethyltetralin feedstock per part of the noble metal component (calculated as the elemental noble metal) of the catalyst by weight per hour.

The catalyst employed in the isomerization step of the method of this invention comprises either beta zeolite or an acidic ultrastable—that is, a thermally stabilized or dealuminated—Y-type crystalline aluminosilicate zeolite having a silica-to-alumina molar ratio of from about 4:1 preferably from about 5:1, to about 10:1, preferably to about 6:1, and having pore windows provided by twelve-membered rings containing oxygen, and a unit cell size of from about 24.2, preferably from about 24.3, to about 24.7, preferably to about 24.6 angstroms. A suitable such zeolite is marketed by Union Carbide under the name LZ-Y72 or LZ-Y20. Water is not detrimental to catalytic activity or selectivity in the isomerization process.

The isomerization catalyst preferably comprises beta zeolite. The composition, structure and preparation of beta zeolite are described in Wadlinger et al., U.S. Pat. No. 3,308,069 which in its entirety is specifically incorporated herein by reference. The structure of beta zeolite is also reported in J. Haggin, "Structure of Zeolite Beta Determined," in Chemical & Engineering News, p. 23 (Jun. 20, 1988). Beta zeolite is also commercially available from PQ Corporation.

The aforesaid ultrastable Y-type zeolite which can be employed in the catalyst for the isomerization step of the method of this invention is in the hydrogen form and contains from about 0.01, preferably from about 1, up to about 5, preferably up to about 3, weight percent of sodium, calculated as elemental sodium and based on the weight of the zeolite.

Preferably the isomerization catalyst comprises a hydrogenation component comprising a Group VIII metal, which more preferably is palladium, platinum or nickel.

The aforesaid zeolite of the isomerization catalyst can be employed either unsupported or supported on a porous refractory, inorganic oxide that is inert under the conditions employed, such as silica, alumina, silica-alumina, magnesia, bentonite or other such clays. If a support is employed, preferably the support comprises silica, alumina or silica-alumina. When a support is employed, the zeolite comprises from about 10, preferably from about 20, to about 90, preferably to about 80 weight percent based on the weight of the catalyst.

If the isomerization is performed on a batch basis, the catalyst is employed at a level in the range of from about 0.1, preferably from about 1.0, to about 5, preferably to about 3 weight percent of the zeolite component of the catalyst, based on the weight of the dimethylnaphthalene feedstock, and the reaction time is from about 0.5, preferably from about 2, to about 10, preferably to about 6 hours. If the isomerization is performed on a continuous basis, the space velocity is in the range of from about 0.1, preferably from about 0.5 to about 20, preferably to about 10 parts of dimethylnaphthalene feedstock per part of zeolite component of the catalyst by weight per hour.

For the dehydrogenation and isomerization reactions described hereinabove, it is preferable to conduct each reaction at the lowest possible reaction temperature that provides for the conversion of a substantial portion of the reaction feedstock to the respective product. At elevated reaction temperatures, coke, tars and other reaction sideproducts tend to form more rapidly and deposit on and deactivate the catalysts disclosed herein. However, regardless of the reaction temperature used, as the catalyst ages catalytic activity typically decreases. This decrease in catalyst activity, which results in reduced feedstock conversion at preselected reaction conditions such as reaction pressure, catalyst level, space velocity and reaction temperature, can be offset somewhat by increasing the reaction temperature. Consequently, a preferred procedure for maximizing the useful life of the dehydrogenation and isomerization catalysts of this invention is to begin using the catalysts at as low a reaction temperature that provides for the conversion of a significant portion of the respective feedstock and then increase the temperature of the reaction as the catalyst ages so as to maintain desirable feedstock conversion levels. For example, when using a batch process, the temperature of the reaction can be raised with each successive batch. When using a continuous process, the reaction temperature of the catalyst bed or continuous stirred tank reactor can be raised as the catalyst ages. When employing an aged dehydrogenation catalyst in the method of this invention, a reaction temperature greater than 300° C. is suitable for maintaining the conversion of a significant portion and preferably at least about 50 wt % and more preferably at least about 70 wt % of the dehydrogenation reaction feedstock to the desired product or products. Preferathrough the reaction mixture to remove oxygen. The temperature of the reaction mixture was raised to the reaction temperature, and periodically samples were removed from the flask and analyzed. Hydrogen generated by the reaction was permitted to vent from the flask during the reaction. The experimental conditions employed, the compositions of the feedstock employed and of the resulting products containing up to 13 carbon atoms, the percent conversion of the feedstock, and the percent selectivity of the formation of desired product from the total amount of feedstock converted in each of Examples 1-6 are presented in Table 1.

The results in Table 1 illustrate that even with the mild temperature and pressure conditions employed in Examples 1-6, the dehydrogenation of the method of this invention affords both excellent conversion and selectivity.

TABLE 1

| | Feed | Example 1 | | Example 2 | | Feed | Ex. 3 | Feed | Ex. 4 | Feed | Ex. 5 | Feed | Ex. 6 |
|---|---|---|---|---|---|---|---|---|---|---|---|---|---|
| Conditions | | | | | | | | | | | | | |
| Hours on stream | | 2.0 | 4.8 | 6.0 | 8.3 | | 8.5 | | 3.0 | | 3.0 | | 6.3 |
| Catalyst cycle no. | | 1 | 1 | 1 | 1 | | 1 | | 1 | | 1 | | 1 |
| Temperature (°C.) | | 242 | 243 | 245 | 244 | | 251 | | 253 | | 254 | | 254 |
| Pressure (psig) | | 1.0 | 1.0 | 1.0 | 1.0 | | 0.0 | | 0.0 | | 0.0 | | 1.0 |
| Feed/catalyst weight ratio | | 10.0 | 10.0 | 50.0 | 50.0 | | 100.0 | | 49.9 | | 100.0 | | 10.0 |
| Compositions (wt %) | | | | | | | | | | | | | |
| 1,4-DMT | 0.0 | 0.0 | 0.0 | 0.0 | 0.0 | | | | | 92.7 | 0.4 | | |
| 1,5-DMT | 92.0 | 2.2 | 0.0 | 4.2 | 1.9 | 93.9 | 1.1 | 0.5 | | | | 1.2 | 0.0 |
| 1,6-DMT | 0.0 | 0.0 | 0.0 | 0.0 | 0.0 | 0.6 | | 0.8 | | | | 55.2 | 0.0 |
| 1,7-DMT | 0.0 | 0.0 | 0.0 | 0.0 | 0.0 | | | 89.4 | 0.4 | | | | |
| 1,8-DMT | 0.0 | 0.0 | 0.0 | 0.0 | 0.0 | | | | | | | 36.0 | 1.4 |
| other DMTs | 0.1 | 0.4 | 0.2 | 0.3 | 0.0 | 1.2 | 0.3 | 0.1 | 0.0 | 0.0 | 3.6 | 1.0 | 0.0 |
| m-xylene | 0.1 | 0.6 | 0.5 | 0.5 | 0.3 | 0.1 | 0.3 | 0.0 | 0.0 | | | | 0.4 |
| non-cyclic | 4.9 | 4.5 | 3.9 | 4.3 | 4.3 | 2.8 | 1.7 | 7.5 | 6.7 | 5.3 | 5.0 | 3.7 | 2.2 |
| Products | | | | | | | | | | | | | |
| 1,3-DMN | 0.0 | 0.0 | 0.0 | 0.0 | 0.0 | | 0.0 | 0.0 | 0.0 | 0.2 | 0.6 | | 0.0 |
| 1,4-DMN | 0.0 | 0.0 | 0.0 | 0.0 | 0.0 | | 0.0 | 0.0 | 0.2 | 1.6 | 90.2 | | 0.0 |
| 1,5-DMN | 0.9 | 89.8 | 93.2 | 88.4 | 92.5 | 0.7 | 94.3 | 0.0 | 0.5 | | | | 1.3 |
| 1,6-DMN | 0.0 | 0.5 | 0.5 | 0.4 | 0.0 | | 0.8 | 0.0 | 0.8 | | | 0.9 | 58.2 |
| 1,7-DMN | 0.0 | 0.0 | 0.0 | 0.0 | 0.0 | | 0.1 | 1.5 | 90.5 | | | | 0.6 |
| 1,8-DMN | 0.0 | 0.0 | 0.0 | 0.6 | 0.2 | 0.0 | | 0.4 | 0.0 | 0.1 | | | 35.6 |
| 2,6 + 2,7-DMNs | 0.0 | 0.0 | 0.0 | 0.0 | 0.0 | | 0.0 | 0.0 | 0.3 | | | | 0.2 |
| Lights | 0.1 | 1.5 | 1.0 | 1.1 | 0.6 | | 0.7 | 0.0 | 0.1 | 0.4 | | | 0.3 |
| Heavies | 0.1 | 0.0 | 0.0 | 0.0 | 0.0 | | 0.0 | 0.0 | 0.0 | | | 1.8 | 0.0 |
| Other | 1.8 | 0.5 | 0.1 | 0.5 | 0.4 | 0.6 | 0.4 | 0.0 | 0.2 | | 0.3 | | 0.0 |
| Total | 100.1 | 100.0 | 100.0 | 100.0 | 100.0 | 100.0 | 100.0 | 99.9 | 99.9 | 100.2 | 100.0 | 99.7 | 100.1 |
| Total DMNs | | 90.3 | 94.3 | 89.0 | 92.5 | | 95.5 | 1.5 | 92.4 | | 90.8 | | 95.8 |
| % Conversion | | 97.6 | 100.0 | 95.4 | 98.0 | | 98.8 | | 99.5 | | 99.5 | | 98.5 |
| % Selectivity | | 99 | 100 | 100 | 101 | | 101 | | 100 | | 96.0 | | 103.4 | bly this temperature is in the range of from about 305° C. to about 500° C., and more preferably in the range of from about 310° C. to about 450° C. When using an aged isomerization catalyst in the method of this invention, a reaction temperature greater than 300° C. is suitable for maintaining the conversion of a significant portion and preferably at least about 20 wt % of the isomerization reaction feedstock to the desired product or products. Preferably this temperature is in the range of from about 305° C. to about 420° C., more preferably in the range of from about 310° C. to about 380° C.

U.S. patent application Ser. No. 316,309 filed on Feb. 27, 1989 is hereby specifically incorporated by reference.

The present invention will be more clearly understood from the following specific examples.

EXAMPLES 1-6

In each of Examples 1-6, the liquid feed and a 5 weight percent palladium-on-carbon catalyst were charged to a flask and nitrogen was continuously passed

EXAMPLES 7-24

In each of Examples 7-24, the particular isomer of dimethylnaphthalene employed as the feed was mixed in liquid form with unsupported catalyst in a stirred reaction vessel with a continuous nitrogen purge to preclude oxygen from the system. The temperature of the reaction vessel was raised to the reaction temperature and samples were withdrawn at various times after commencement of the reaction and analyzed. The conditions employed, the compositions of the feedstock employed and of the resulting products containing up to 13 carbon atoms, the percent conversion of the feedstock, and the percent selectivity of the formation of desired product from the total amount of feedstock converted in each of Examples 7-24 are presented in Table 2.

The catalyst employed in Example 7 was a crystalline borosilicate molecular sieve (HAMS-1B from Amoco Chemical). The catalyst employed in Example 8 was Union Carbide's LZ-Y20 ultrastable Y-type sieve, containing 2 weight percent of copper, calculated as elemental copper. The catalyst employed in Example 9 was Union Carbide's LZ-Y62, a non-ultrastable, Y-type sieve in the ammonia exchanged form and having a unit cell size of 24.73 Å. The catalyst employed in Examples 10 and 11 was commercially available Union Carbide's LZ-Y82, an ultra-stable-molecular sieve having a unit cell size of 24.56 Å and a sodium content of less than 0.2 weight percent. In Example 10, the sieve was in the ammonia form and had not been calcined. In Example 11, the sieve had been calcined to form the hydrogen form. The catalyst employed in Example 12 was a commercially available amorphous silica-alumina containing 13 weight percent of alumina. The catalyst employed in Example 13 was commercially available mordenite in the acid form. The catalyst employed in Examples 14, 15 and 17-22 was commercially available Union Carbide's LZ-Y72 in the hydrogen form as received from the manufacturer. The catalyst employed in Example 16 was commercially available Grace USY sieve containing 2.6 weight percent of sodium and has chemical and physical properties that are very similar to those of Union Carbide's LZ-Y72, and is also suitable for use as a catalyst in either the cyclization or isomerization step in the method of this invention. 1,5-dimethylnaphthalene was the feed in Examples 7-21. The feed was 1,7-dimethylnaphthalene in Example 22 and 1,4-dimethylnaphthalene in Examples 23 and 24. For the purposes of Table 2, the concentration of 2,7-DMN in the product is taken to be approximately equal to the concentration of 1,7-DMN and is subtracted from the sum of 2,6-DMN and 2,7-DMN (which are determined together) for the purpose of determining the concentration of 2,6-DMN alone. The effective maximum concentrations of a particular desired DMN in its triad is its equilibrium concentration in the triad, which generally is 40-45 weight percent.

TABLE 2

| | Feed | Ex. 7 | Feed | Ex. 8 | Feed | Ex. 9 | Ex. 10 | Ex. 11 | Ex. 12 | Ex. 13 |
|---|---|---|---|---|---|---|---|---|---|---|
| Conditions | | | | | | | | | | |
| Temperature (°C.) | | 249 | | 243 | | 248 | 249 | 240 | 233 | 248 |
| Pressure (psig) | | 1 | | 1 | | 1 | 1 | 1 | 1 | 1 |
| Catalyst | | Amsac-3400 | | LZ-20 2% Cu | | LZ-Y62 | LZ-Y82[1] | LZ-Y82[2] | $SiO_2/Al_2O_3$[3] | Mordenite[4] |
| Feed/catalyst wt ratio | | 10 | | 10 | | 10.0 | 9.9 | 9.8 | 10.1 | 9.8 |
| Hours on stream | | 7.3 | | 13 | | 12 | 11.8 | 5.5 | 13 | 11.5 |
| Product Composition (wt %) | | | | | | | | | | |
| 1,2-DMN | 0.0 | 0.0 | 0.0 | 0.1 | 0.0 | 0.0 | 0.0 | 0.4 | 0.0 | 0.0 |
| 1,3-DMN | 0.0 | 0.0 | 0.0 | 0.0 | 0.0 | 0.0 | 0.0 | 0.0 | 0.0 | 0.0 |
| 1,4-DMN | 0.0 | 0.0 | 0.0 | 0.0 | 0.0 | 0.0 | 0.0 | 0.0 | 0.0 | 0.0 |
| 1,5-DMN | 93.4 | 69.3 | 82.6 | 8.7 | 82.6 | 82.3 | 75.6 | 4.1 | 21.9 | 41.2 |
| 1,6-DMN | 0.0 | 20.1 | 11.8 | 37.8 | 11.8 | 12.1 | 18.3 | 25.4 | 42.8 | 29.4 |
| 1,7-DMN | 0.0 | 0.0 | 1.2 | 1.5 | 1.2 | 1.3 | 1.2 | 3.6 | 1.2 | 0.7 |
| 2,3-DMN | 0.0 | 0.0 | 0.0 | 0.0 | 0.0 | 0.0 | 0.0 | 1.2 | 0.0 | 0.0 |
| 2,6- + 2,7-DMNs | 0.0 | 5.4 | 1.8 | 36.3 | 1.8 | 2.1 | 3.2 | 30.4 | 29.3 | 27.6 |
| Lights | 6.3 | 2.6 | 1.7 | 1.4 | 1.7 | 1.8 | 1.2 | 1.3 | 1.2 | 1.0 |
| Heavies | 0.0 | 1.9 | 0.2 | 5.8 | 0.2 | 0.1 | 0.1 | 16.2 | 1.2 | 0.0 |
| Naphthalene | 0.0 | 0.0 | 0.0 | 0.1 | 0.0 | 0.0 | 0.0 | 0.7 | 0.0 | 0.0 |
| Methylnaphthalenes | 0.0 | 0.2 | 0.6 | 6.5 | 0.6 | 0.3 | 0.2 | 12.7 | 2.0 | 0.1 |
| Other | 0.2 | 0.5 | 0.0 | 1.9 | 0.0 | 0.0 | 0.0 | 3.9 | 0.5 | 0.0 |
| Total | 99.9 | 100.0 | 99.9 | 100.1 | 99.6 | 100.1 | 99.8 | 100.1 | 100.1 | 100.0 |
| Total DMNs | 93.4 | 94.8 | 97.3 | 84.4 | 97.3 | 97.8 | 98.3 | 65.1 | 95.2 | 98.9 |
| 2,7-DMN % | | | | | | | | | | |
| 2,6-DMN % in the 1,5-, 1,6- and 2,6-DMN triad | 0.0 | 5.7 | 0.6 | 42.8 | 0.6 | 0.9 | 2.1 | 47.7 | 30.3 | 27.6 |
| 2,6-DMN selectivity | | 100 | | 71.7 | | | | 40.5 | 93.1 | >100 |

Footnotes
[1] not calcined
[2] calcined
[3] 13% $Al_2O_3$
[4] in H form

| | Ex. 14 | Ex. 15 | Ex. 16 | Ex. 17 | Ex. 18 | Ex. 19 | Ex. 20 | Ex. 21 |
|---|---|---|---|---|---|---|---|---|
| Conditions | | | | | | | | |
| Temperature (°C.) | 226 | 227 | 252 | 251 | 248 | 248 | 249 | 248 |
| Pressure (psig) | 1 | 1 | 1 | 1 | 1 | 1 | 1 | 1 |
| Catalyst | LZY-72 | LZY-72 | US-Y[5] | LZY-72 | LZY-72 | LZY-72 | LZY-72 | LZY-72 |
| Feed/catalyst wt ratio | 50.4 | 50.4 | 50.8 | 50.6 | 50.6 | 50.6 | 50.6 | 50.6 |
| Hours on stream | 19.5 | 23.3 | 11.5 | 3.0 | 4.8 | 6.8 | 8.5 | 10.5 |
| Product Composition (wt %) | | | | | | | | |
| 1,2-DMN | 0.0 | 0.0 | 0.0 | 0.0 | 0.0 | 0.0 | 0.0 | 0.0 |
| 1,3-DMN | 0.0 | 0.0 | 0.0 | 0.0 | 0.0 | 0.0 | 0.0 | 0.0 |
| 1,4-DMN | 0.0 | 0.0 | 0.0 | 0.0 | 0.0 | 0.0 | 0.0 | 0.0 |
| 1,5-DMN | 24.0 | 21.3 | 17.5 | 20.9 | 15.1 | 12.2 | 9.6 | 8.7 |
| 1,6-DMN | 39.9 | 40.3 | 41.5 | 41.6 | 41.6 | 41.6 | 40.0 | 39.7 |
| 1,7-DMN | 1.0 | 0.9 | 1.0 | 0.9 | 1.0 | 1.0 | 1.2 | 1.2 |
| 2,3-DMN | 0.0 | 0.0 | 0.0 | 0.0 | 0.0 | 0.0 | 0.0 | 0.0 |
| 2,6- + 2,7-DMNs | 31.8 | 34.2 | 35.9 | 32.9 | 37.6 | 40.0 | 43.0 | 43.3 |
| Lights | 1.9 | 0.9 | 1.2 | 1.6 | 1.6 | 1.2 | 1.0 | 1.1 |
| Heavies | 0.9 | 1.1 | 1.0 | 0.8 | 1.1 | 1.6 | 2.1 | 2.2 |
| Naphthalene | 0.0 | 0.0 | 0.0 | 0.0 | 0.0 | 0.0 | 0.0 | 0.0 |
| Methylnaphthalenes | 1.0 | 1.1 | 1.3 | 1.1 | 1.5 | 1.7 | 2.6 | 2.8 |
| Other | 0.4 | 0.2 | 0.5 | 0.3 | 0.5 | 0.7 | 0.5 | 0.9 |
| Total | 100.9 | 100.0 | 99.9 | 100.1 | 100.0 | 100.0 | 100.0 | 99.9 |
| Total DMNs | 96.7 | 96.7 | 95.9 | 96.3 | 95.2 | 94.8 | 93.9 | 93.0 |

TABLE 2-continued

| | | | | | | | | |
|---|---|---|---|---|---|---|---|---|
| 2,7-DMN % | 1.1 | | 1.1 | | | | | 1.6 |
| 2,6-DMN % in the 1,5-, 1,6- and 2,6-DMN triad | 32.5 | 35.1 | 37.2 | 33.8 | 39.2 | 42.0 | 45.7 | 46.5 |
| 2,6-DMN selectivity | 99.5 | 99.9 | 97.3 | 98.4 | 95.6 | 94.6 | 92.3 | 90.5 |

Footnote
²ultrastable sieve containing 2.6% Na

| | Feed | Ex. 22 | Feed | Ex. 23 | Ex. 24 |
|---|---|---|---|---|---|
| Conditions | | | | | |
| Temperature (°C.) | | 251 | | 247 | 252 |
| Pressure (psig) | | 1 | | 1 | 1 |
| Catalyst | LZY-72 | LZY-72 | LZY-72 | LZY-72 | LZY-72 |
| Feed/catalyst wt ratio | | 50.0 | | 44.0 | 44.0 |
| Hours on stream | | 4.0 | | 2.0 | 6.5 |
| Product Composition (wt %) | | | | | |
| 1,2-DMN | 0.0 | 0.0 | 0.0 | 0.1 | 0.4 |
| 1,3-DMN | 0.0 | 0.0 | 0.6 | 50.8 | 51.0 |
| 1,4-DMN | 0.0 | 0.0 | 90.6 | 15.1 | 9.0 |
| 1,5-DMN | 0.5 | 0.2 | 0.0 | 0.0 | 0.0 |
| 1,6-DMN | 0.7 | 1.4 | 0.0 | 0.0 | 0.0 |
| 1,7-DMN | 90.4 | 40.5 | 0.0 | 0.0 | 0.1 |
| 2,3-DMN | 0.0 | 0.0 | 0.0 | 22.1 | 23.3 |
| 2,6-DMN | 0.0 | 1.3 | 0.0 | 0.0 | 0.3 |
| 2,7-DMN | 0.3 | 44.7 | 0.0 | 0.0 | 0.1 |
| Lights | 6.6 | 6.3 | 5.2 | 4.3 | 3.6 |
| Heavies | 0.0 | 0.7 | 0.0 | 1.8 | 3.8 |
| Naphthalene | | | 0.0 | 2.0 | 3.3 |
| Methylnaphthalenes | 0.2 | 1.7 | 3.6 | 3.9 | 4.8 |
| Other | 1.3 | 2.8 | 0.0 | 0.0 | 0.3 |
| Total | 100.0 | 99.6 | 100.0 | 100.1 | 100.0 |
| Total DMNs | 92.0 | 88.4 | 91.1 | 88.1 | 84.2 |
| % desired DMN[1] in its triad | 0.3 | 52.2 | 0.6 | 25.1 | 28.0 |
| Selectivity | | 89.0 | | 87.5 | 74.8 |

[1]2,7-DMN in Example 22 and 2,3-DMN in Examples 23-24.

EXAMPLE 25

7.5 kilograms of distilled water, 7.5 kilograms of an aqueous solution containing 40 weight percent of tetraethylamine hydroxide, 50 grams of sodium hydroxide and 300 grams of sodium aluminate were stirred and dissolved in a 25-gallon stainless steel tank. The resulting solution and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, dried at 120° C. and then calcined at 538° C. for 4 hours.

The resulting dried powder contained 0.37 weight percent of sodium, calculated as elemental sodium, and x-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
|---|---|
| 4.18 | 16.2 |
| 3.99 | 100.0 |
| 3.54 | 6.1 |
| 3.35 | 12.6 |
| 3.11 | 3.0 |
| 3.05 | 14.6 |
| 2.94 | 5.3 |
| 2.69 | 4.1 |
| 2.54 | 1.5 |
| 2.08 | 11.5 |

The powder was employed as the catalyst without being ion-exchanged Some powder was ion-exchanged using the ion-exchange procedure of Example 27 to reduce the sodium content, and after being ion-exchanged, the powder's alumina content, silica-to-alumina mole ratio and silicon-to-aluminum atom ratio were measured as 1.14 weight percent, 68:1 and 34:1, respectively.

EXAMPLE 26

8 kilograms of distilled water, 8 kilograms of an aqueous solution containing 40 weight percent of tetraethylamine hydroxide, 3.81 kilograms of an aqueous solution containing 20 weight percent of tetraethylamine hydroxide, 0.6 kilogram of sodium aluminate, and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, dried at 120° C. for about 16 hours and then calcined at 538° C. for 6 hours The resulting dried powder contained 0.17 weight percent of sodium, calculated as elemental sodium. X-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
|---|---|
| 4.19 | 17.7 |
| 4.01 | 100.0 |
| 3.54 | Weak |
| 3.35 | 13.8 |
| 3.11 | Weak |
| 3.05 | 13.4 |
| 2.95 | 2.8 |
| 2.67 | Weak |
| 2.49 | 0.6 |
| 2.09 | 7.6 |

The powder was employed as the catalyst without being ion-exchanged. After being ion-exchanged using the procedure of Example 27 in order to reduce the sodium content, the powder's silica-to-alumina mole ratio and silicon-to-aluminum atom ratio were measured as 30:1 and 14.8:1, respectively.

EXAMPLE 27

2.3 kilograms of the un-ion-exchanged catalyst powder produced in Example 26, 4 kilograms of distilled water, and 12 kilograms of an aqueous solution containing 19 weight percent of ammonium nitrate were stirred in a 22-liter flask at 72° C. for 4 hours. The mixture was then cooled; the liquid was removed by decantation, and the resulting ion-exchanged catalyst was then washed with water. The catalyst was then dried at 120° C. and calcined at 538° C. for 3 hours. The ion-exchanged catalyst contained 0.01 weight percent of sodium (calculated as elemental sodium), 2.43 weight percent of aluminum (calculated as elemental aluminum), and a silica-to-alumina mole ratio and a silicon-to-aluminum atomic ratio of 30:1 and 14.8:1, respectively.

163 grams of this dry, ion-exchanged beta zeolite powder, 454 grams of an alumina sol containing 8.8 weight percent of solids, and 123 grams of distilled water were blended to obtain a smooth, uniform slurry. The slurry was maintained at 23° C. for 5 hours to permit liquid to evaporate from the slurry. The slurry was then dried at 120° C. for about 16 hours and calcined at 538° C. for 2 hours, to afford solids containing 80 weight percent of beta zeolite and 20 weight percent of alumina, which were then ground and sieved to form particles having a 20-40 mesh size.

EXAMPLES 28-46

In each of Examples 28-46, the particular feedstock employed was mixed in liquid form with a catalyst in a stirred reaction vessel with a continuous nitrogen purge to preclude oxygen from the system. The weight ratio of the feedstock-to-zeolite component of the catalyst was 49:1 in each case. The pressure of the contents of the reaction vessel was maintained at about 1 pound per square inch gauge. The temperature of the reaction vessel was raised to the reaction temperature and samples were withdrawn at various times after commencement of the reaction and analyzed. The conditions employed, the compositions of the feedstock employed and of the resulting products, the percent of the 1,5-, 1,6- and 2,6-DMN triad in each thereof, the percent of 2,6-DMN in each such 1,5-, 1,6- and 2,6-DMN triad, the percent decreases in each 1,5-, 1,6- and 2,6-DMN triad, the percent gain in each 1,7-, 1-8- and 2,7-DMN triad and the percent gain in total methylnaphthalene and trimethylnaphthalene content in each of Examples 28-46 are presented in Tables 3-7.

The catalyst employed in Examples 28-30 was commercially available Union Carbide's unsupported LZ-Y72 in the hydrogen form as received from the manufacturer. The catalyst employed in Examples 31-34 was an unsupported beta zeolite having a relatively high silicon-to-aluminum ratio and prepared by the procedure of Example 25. The catalyst employed in Examples 35-43 was an unsupported beta zeolite having a relatively low silicon-to-aluminum ratio and prepared by the procedure of Example 26. A single sample of this catalyst was used for four cycles in Examples 38-43. The catalyst employed in Examples 44-46 was also the beta zeolite having the relatively low silicon-to-aluminum ratio and prepared by the procedure of Example 26, but in this instance was ion-exchanged to reduce the sodium content and supported on an alumina matrix by the procedure of Example 27.

TABLE 3

| | Feed | Ex. 28 | Ex. 29 | Ex. 30 |
|---|---|---|---|---|
| Conditions | | | | |
| Catalyst | | LZ-Y72 | LZ-Y72 | LZ-Y72 |
| Temperature (°C.) | | 250 | 250 | 250 |
| Hours on Stream | | 1 | 3 | 4.75 |
| Product Composition (wt %) | | | | |
| 1,5-DMN | 91.03 | 38.70 | 18.30 | 12.84 |
| 1,6-DMN | 3.73 | 36.92 | 40.67 | 40.35 |
| 2,6-DMN | 0 | 18.42 | 32.40 | 36.18 |
| 1,7-DMN | 0.74 | 0.81 | 0.93 | 1.08 |
| 2,7-DMN | 0 | 0.73 | 1.37 | 1.81 |
| Methylnaphthalenes | 0.06 | 0.62 | 1.43 | 2.03 |
| Trimethylnaphthalenes | 0.44 | 0.53 | 1.33 | 2.02 |
| Other | 4.00 | 3.27 | 3.57 | 3.69 |
| Total | 100.00 | 100.00 | 100.00 | 100.00 |
| 1,5-, 1,6- and 2,6-DMN triad content | 94.76 | 94.04 | 91.37 | 89.37 |
| 2,6-DMN percent in 1,5-, 1,6- and 2,6-DMN triad | 0 | 19.59 | 35.46 | 40.49 |
| 1,5-, 1,6- and 2,6-DMN triad percent loss | 0 | 0.72 | 3.39 | 5.39 |
| 1,7-, 1,8- and 2,7-DMN triad percent gain | 0 | 0.80 | 1.56 | 2.15 |
| Methylnaphthalene and trimethylnaphthalene percent gain | 0 | 0.71 | 2.32 | 3.61 |

TABLE 4

| | Feed | Ex. 31 | Ex. 32 | Ex. 33 | Ex. 34 |
|---|---|---|---|---|---|
| Conditions | | | | | |
| Catalyst from Example | | 25 | 25 | 25 | 25 |
| Temperature (°C.) | | 250 | 250 | 250 | 250 |
| Hours on Stream | | 1 | 3 | 5 | 7 |
| Product Composition (wt %) | | | | | |
| 1,5-DMN | 91.03 | 54.00 | 28.93 | 18.94 | 14.09 |
| 1,6-DMN | 3.73 | 28.76 | 37.62 | 39.70 | 40.41 |
| 2,6-DMN | 0 | 12.91 | 28.76 | 35.96 | 39.55 |
| 1,7-DMN | 0.74 | 0.61 | 0.58 | 0.60 | 0.67 |
| 2,7-DMN | 0 | 0.67 | 1.09 | 1.13 | 1.28 |
| Methylnaphthalenes | 0 | 0.12 | 0.29 | 0.41 | 0.57 |
| Trimethylnaphthalenes | 0.44 | 0.10 | 0.19 | 0.34 | 0.46 |
| Other | 4.06 | 2.83 | 2.67 | 2.92 | 2.97 |
| Total | 100.00 | 100.00 | 100.00 | 100.00 | 100.00 |
| 1,5-, 1,6- and 2,6-DMN triad content | 94.76 | 95.67 | 95.18 | 94.60 | 94.05 |
| 2,6-DMN percent in 1,5-, 1,6- and 2,6-DMN triad | 0 | 13.49 | 30.08 | 38.01 | 42.05 |
| 1,5-, 1,6- and 2,6-DMN triad percent loss | 0 | −0.91 | −0.42 | 0.16 | 0.71 |
| 1,7-, 1,8- and 2,7-DMN triad percent gain | 0 | 0.54 | 0.93 | 0.99 | 1.21 |
| Methylnaphthalene and trimethylnaphthalene percent gain | 0 | −0.23 | 0.04 | 0.31 | 0.59 |

TABLE 5

| | Feed | Ex. 35 | Ex. 36 | Ex. 37 |
|---|---|---|---|---|
| Conditions | | | | |
| Catalyst from Example | | 26 | 26 | 26 |
| Temperature (°C.) | | 250 | 250 | 250 |
| Hours on Stream | | 1.25 | 3 | 5 |
| Product Composition (wt %) | | | | |
| 1,5-DMN | 91.03 | 21.94 | 10.79 | 8.20 |

TABLE 5-continued

|  | Feed | Ex. 35 | Ex. 36 | Ex. 37 |
|---|---|---|---|---|
| 1,6-DMN | 3.73 | 38.62 | 40.89 | 41.20 |
| 2,6-DMN | 0 | 35.59 | 43.28 | 44.94 |
| 1,7-DMN | 0.74 | 0.52 | 0.60 | 0.64 |
| 2,7-DMN | 0 | 0.30 | 0.53 | 0.47 |
| Methylnaphthalenes | 0 | 0.33 | 0.59 | 0.84 |
| Trimethylnaphthalenes | 0.44 | 0.16 | 0.46 | 0.78 |
| Other | 4.06 | 2.54 | 2.86 | 2.93 |
| Total | 100.00 | 100.00 | 100.00 | 100.00 |
| 1,5-, 1,6- and 2,6-DMN triad content | 94.76 | 96.15 | 94.96 | 94.34 |
| 2,6-DMN percent in 1,5-, 1,6- and 2,6-DMN triad | 0 | 37.02 | 45.58 | 47.63 |
| 1,5-, 1,6- and 2,6-DMN triad percent loss | 0 | −1.39 | −0.20 | 0.42 |
| 1,7-, 1,8- and 2,7-DMN triad percent gain | 0 | 0.08 | 0.39 | 0.37 |
| Methylnaphthalene and trimethylnaphthalene percent gain | 0 | 0.05 | 0.61 | 1.18 |

TABLE 6

|  | Feed | Ex. 38 | Ex. 39 | Ex. 40 | Feed | Ex. 41 | Ex. 42 | Ex. 43 |
|---|---|---|---|---|---|---|---|---|
| Conditions | | | | | | | | |
| Catalyst from Example | | 26 | 26 | 26 | | 26 | 26 | 26 |
| Temperature (°C.) | | 240 | 240 | 240 | | 240 | 265 | 265 |
| Hours on Stream | | 3 | 3.9 | 3 | | 4.5 | 3 | 4.5 |
| Catalyst Cycle | | 1st | 1st | 3rd | | 3rd | 4th | 4th |
| Product Composition (wt %) | | | | | | | | |
| 1,5-DMN | 88.14 | 9.63 | 7.99 | 26.62 | 88.14 | 17.73 | 11.47 | 8.16 |
| 1,6-DMN | 3.66 | 39.45 | 39.53 | 35.39 | 3.66 | 38.10 | 39.23 | 39.73 |
| 2,6-DMN | 0 | 41.50 | 42.34 | 29.83 | 0 | 36.25 | 40.02 | 42.31 |
| 1,7-DMN | 0.74 | 0.66 | 0.69 | 0.57 | 0.74 | 0.59 | 0.66 | 0.72 |
| 2,7-DMN | 0 | 1.26 | 1.50 | 1.02 | 0 | 0.97 | 1.20 | 1.13 |
| Methylnaphthalenes | 0.13 | 0.99 | 1.17 | 0.26 | 0.13 | 0.33 | 0.48 | 0.70 |
| Trimethylnaphthalenes | 0.54 | 0.53 | 0.70 | 0.17 | 0.54 | 0.29 | 0.37 | 0.52 |
| Other | 6.79 | 5.98 | 6.08 | 6.14 | 6.79 | 5.74 | 6.57 | 6.73 |
| Total | 100.00 | 100.00 | 100.00 | 100.00 | 100.00 | 100.00 | 100.00 | 100.00 |
| 1,5-, 1,6- and 2,6-DMN triad content | 91.80 | 90.58 | 89.86 | 91.84 | 91.80 | 92.08 | 90.72 | 90.20 |
| 2,6-DMN percent in 1,5-, 1,6- and 2,6-DMN triad | 0 | 45.82 | 47.12 | 32.48 | 0 | 39.37 | 44.11 | 46.91 |
| 1,5-, 1,6- and 2,6-DMN triad percent loss | 0 | 1.22 | 1.94 | −0.04 | 0 | −0.28 | 1.08 | 1.60 |
| 1,7-, 1,8- and 2,7-DMN triad percent gain | 0 | 1.18 | 1.45 | 0.85 | 0 | 0.82 | 1.12 | 1.11 |
| Methylnaphthalene and trimethylnaphthalene percent gain | 0 | 0.85 | 1.20 | −0.24 | 0 | −0.05 | 0.18 | 0.55 |

TABLE 7

|  | Feed | Ex. 44 | Ex. 45 | Ex. 46 |
|---|---|---|---|---|
| Conditions | | | | |
| Catalyst from Example | | 27 | 27 | 27 |
| Temperature (°C.) | | 250 | 250 | 250 |
| Hours on Stream | | 1 | 2 | 3 |
| Product Composition (wt %) | | | | |
| 1,5-DMN | 88.14 | 16.50 | 11.20 | 9.23 |
| 1,6-DMN | 3.66 | 38.10 | 39.30 | 39.70 |
| 2,6-DMN | 0 | 37.42 | 41.07 | 42.15 |
| 1,7-DMN | 0.74 | 0.53 | 0.55 | 0.58 |
| 2,7-DMN | 0 | 0.97 | 0.84 | 1.00 |
| Methylnaphthalenes | 0.13 | 0.52 | 0.69 | 0.83 |
| Trimethylnaphthalenes | 0.54 | 0.32 | 0.62 | 0.75 |
| Other | 6.79 | 5.64 | 5.73 | 5.76 |
| Total | 100.00 | 100.00 | 100.00 | 100.00 |
| 1,5-, 1,6- and 2,6-DMN triad content | 91.80 | 92.02 | 91.57 | 91.08 |
| 2,6-DMN percent in 1,5-, 1,6- and 2,6-DMN triad | 0 | 40.67 | 44.85 | 46.28 |
| 1,5-, 1,6- and 2,6-DMN triad percent loss | 0 | −0.22 | 0.23 | 0.72 |
| 1,7-, 1,8- and 2,7-DMN triad percent gain | 0 | 0.76 | 0.65 | 0.84 |
| Methylnaphthalene and trimethylnaphthalene percent gain | 0 | 0.17 | 0.64 | 0.91 |

Comparison of the results in Tables 3–7 illustrates clearly that (1) the use of a beta zeolite catalyst affords reduced losses of the 1,5-, 1,6- and 2,6-dimethylnaphthalene triad, reduced formation of methylnaphthalenes, trimethylnaphthalenes and the 1,7-, 1,8- and 2,7-dimethylnaphthalene triad relative to the use of the LZ-Y72 zeolite catalyst; and (2) the use of a beta zeolite catalyst either unsupported or supported on a base material and having a relatively lower silicon-to-aluminum ratio affords greater formation of 2,6-dimethylnaphthalene and reduced losses of the 1,5-, 1,6- and 2,6-dimethylnaphthalene triad relative to the use of a beta zeolite catalyst having a relatively higher silicon-to-aluminum ratio and permits the use of lower reaction temperatures or the use at a higher temperature of even a partially deactivated catalyst relative to the use of a LZ-Y72 zeolite catalyst.

EXAMPLES 47–54

In each of Examples 47–54 a fixed bed reactor was used to evaluate a continuous process for the dehydrogenation of a feedstock containing 1,5-dimethyltetralin (1,5-DMT) to yield mainly 1,5-dimethylnaphthalene (1,5-DMN). The fixed bed reactor used was a 13 centimeter long stainless steel tube having a 0.20 centimeter inside diameter and packed with 3.15 grams of a catalyst containing 0.35 wt % platinum and 0.35 wt. % rhenium on a 16–25 mesh gamma alumina support. Preheated feedstocks having the compositions shown in Tables 8 and 9 were pumped upflow through the catalyst bed in the reactor tube at the reaction conditions listed in Tables 8 and 9, respectively. Thermocouples installed in the reactor inlet and exit monitored the reaction temperature. Heating tape wrapped around the reactor tube was used to maintain the set reaction temperature. Reaction pressure was maintained to keep the feedstock and hydrocarbon products as liquids. Reactor effluent was collected in a 300 ml pressure vessel maintained at 70°-100° C. to keep the product mixture liquid. The hydrogen gas generated by the dehydrogenation reaction was vented continuously from the collection vessel through a pressure regulator.

The selectivity and conversion percentages presented in Tables 8 and 9 were calculated according to the following equations: (1,6-DMN is in the 1,5-, 1,6-, 2,6-DMN triad and can be isomerized to 2,6-DMN; consequently, 1,6-DMT and 1,6-DMN wt. percentages are included in the following equations.)

$$\% \text{ Selectivity} = \frac{[(\text{wt } \% \text{ 1,5 } + \text{ 1,6-DMN in product}) - (\text{wt } \% \text{ 1,5 } + \text{ 1,6-DMN in feed})] \times 100}{(\text{wt } \% \text{ 1,5 } + \text{ 1,6-DMT in feed}) - (\text{wt } \% \text{ 1,5 } + \text{ 1,6-DMT in product})}$$

$$\% \text{ Conversion} = \frac{[(\text{wt } \% \text{ 1,5 } + \text{ 1,6-DMT in feed}) - (\text{wt } \% \text{ 1,5 } + \text{ 1,6-DMT in product})] \times 100}{(\text{wt } \% \text{ 1,5 } + \text{ 1,6-DMT in feed})}$$

Table 8 reports data for the single-pass conversion of the 1,5-DMT containing feedstock to 1,5-DMN containing product. Table 9 reports data for the single-pass conversion of a 1,5-DMT containing feedstock that was distilled to remove heavy components before subjecting the feedstock to the dehydrogenation reaction. Table 9 also reports data for a two-pass conversion of the 1,5-DMT containing feedstock. In the two-pass conversion procedure the product stream from the single-pass dehydrogenation reaction was collected and passed through the fixed bed dehydrogenation reactor a second time. This two-pass procedure simulates a process utilizing two or more fixed bed dehydrogenation reactors in series wherein the hydrogen formed by the dehydrogenation reaction is partially or totally vented between reactors.

TABLE 9

| | Feed | Ex. 53 (1st pass) | Ex. 54 (2nd pass) | Overall |
|---|---|---|---|---|
| Condition | | | | |
| Hours on stream | | 477 | 740 | |
| Catalyst cycle no. | | 3 | 3 | |
| Temperature (°C.) | | 400 | 401 | |
| Pressure (psig) | | 200 | 200 | |
| WHSV (grams feed/hr/gram catalyst) | | 4.30 | 4.36 | |
| Composition (wt %) | | | | |
| 1,5-DMT | 83.16 | 7.78 | 1.05 | |
| 1,6-DMT | 2.79 | 0.20 | 0.04 | |
| 2,6- + 2,7- + 1,7-DMT | 0.87 | 0.06 | 0.00 | |
| 2,8-DMT | 0.82 | 0.45 | 0.06 | |
| 2,5- + 1,8-DMT | 0.87 | 0.20 | 0.05 | |
| Lights | 0.46 | 1.34 | 1.49 | |
| $C_{12}$ Indane | 1.52 | 1.71 | 1.65 | |
| o-Tolylpentane | 4.88 | 5.04 | 4.67 | |
| Products | | | | |
| 1,5-DMN | 2.02 | 76.00 | 79.30 | |
| 1,6-DMN | 0.36 | 4.51 | 7.17 | |
| 1,7-DMN | 0.03 | 0.88 | 1.24 | |
| 1,8-DMN | 0.01 | 0.17 | 0.12 | |
| 2,6- + 2,7-DMN | 0.08 | 0.18 | 0.33 | |
| 1-Methylnaphthalene | 0.00 | 0.28 | 1.19 | |
| 2-Methylnaphthalene | 0.06 | 0.01 | 0.05 | |
| Heavies | 0.17 | 0.45 | 0.80 | |
| Others | 1.70 | 0.75 | 0.78 | |
| Total | 100.00 | 100.00 | 100.00 | |
| % Conversion | — | 90.7 | 86.4 | 98.7 |
| % Selectivity | — | 100.0 | 86.5 | 98.9 |

Examples 47-54 demonstrate that high conversions are possible at a wide range of flow rates (WHSV) of from about 0.54 to about 4.14 grams of feed per gram of catalyst per hour using a continuous dehydrogenation procedure. As the flow rates increase the conversion decreases; however, the selectivity to 1,5- and 1,6-DMN increases. Example 51 and 52 demonstrate that even after many hours of liquid phase operation high conversion and selectivities are maintained at a reaction

TABLE 8

| | Feed | Ex. 47 | Ex. 48 | Ex. 49 | Ex. 50 | Ex. 51 | Ex. 52 |
|---|---|---|---|---|---|---|---|
| Conditions | | | | | | | |
| Hours on stream | | 436 | 441 | 482 | 503 | 957 | 1223 |
| Catalyst cycle no. | | 2 | 2 | 2 | 2 | 2 | 2 |
| Temperature (°C.) | | 401 | 400 | 400 | 401 | 400 | 400 |
| Pressure (psig) | | 201 | 201 | 202 | 201 | 170 | 178 |
| WHSV (grams feed/hr/gram catalyst) | | 4.14 | 2.07 | 0.54 | 1.07 | 2.12 | 2.13 |
| Composition (wt %) | | | | | | | |
| 1,5-DMT | 84.66 | 4.56 | 3.90 | 1.90 | 3.51 | 3.17 | 7.59 |
| 1,6-DMT | 0.91 | 0.07 | 0.12 | 0.21 | 0.15 | 0.06 | 0.09 |
| 2,6- + 2,7- + 1,7-DMT | 0.27 | 0.00 | 0.00 | 0.06 | 0.00 | 0.00 | 0.00 |
| 2,8-DMT | 0.68 | 0.31 | 0.16 | 0.00 | 0.16 | 0.20 | 0.00 |
| 2,5- + 1,8-DMT | 0.31 | 0.00 | 0.11 | 0.22 | 0.00 | 0.08 | 0.23 |
| Lights | 0.24 | 1.68 | 2.36 | 9.61 | 3.31 | 2.05 | 1.54 |
| $C_{12}$ Indane | 1.06 | 1.70 | 2.10 | 2.08 | 2.56 | 1.82 | 1.78 |
| o-Tolylpentane | 3.20 | 3.68 | 3.78 | 2.48 | 3.74 | 3.78 | 3.77 |
| Products | | | | | | | |
| 1,5-DMN | 1.64 | 80.15 | 77.48 | 51.95 | 71.46 | 78.97 | 75.68 |
| 1,6-DMN | 0.07 | 2.37 | 4.18 | 11.20 | 6.54 | 3.72 | 3.09 |
| 1,7-DMN | 0.00 | 0.42 | 0.62 | 1.29 | 0.78 | 0.59 | 0.50 |
| 1,8-DMN | 0.00 | 0.18 | 0.11 | 0.04 | 0.04 | 0.05 | 0.18 |
| 2,6- + 2,7-DMN | 0.00 | 0.00 | 0.10 | 0.79 | 0.23 | 0.09 | 0.16 |
| 1-Methylnaphthalene | 0.00 | 0.57 | 1.15 | 7.60 | 2.09 | 0.79 | 0.65 |
| 2-Methylnaphthalene | 0.00 | 0.00 | 0.00 | 0.29 | 0.10 | 0.06 | 0.05 |
| Heavies | 6.69 | 3.38 | 2.23 | 2.08 | 2.48 | 2.23 | 2.18 |
| Others | 0.27 | 0.94 | 1.62 | 8.22 | 2.85 | 2.33 | 2.52 |
| Total | 100.00 | 100.00 | 100.00 | 100.00 | 100.00 | 100.00 | 100.00 |
| % Conversion | — | 94.6 | 95.3 | 97.5 | 95.7 | 96.2 | 91.0 |
| % Selectivity | — | 99.8 | 98.0 | 73.6 | 93.1 | 98.3 | 98.9 | temperature of about 400° C. Noble metal catalysts in general require the addition of large amounts of hydrogen to maintain catalytic activity for prolonged periods. However, by employing reaction conditions in the dehydrogenation method of this invention such that a liquid reaction mixture was maintained, additional hydrogen was not required to maintain catalyst activity. In commercial operation, expensive hydrogen recycle equipment would not, therefore, be required. Examples 53 and 54 demonstrate that the continuous dehydrogenation reaction can be run in at least a two-pass process wherein the product stream from the first pass through the reactor, after the removal of hydrogen, is feed to a second fixed bed reactor. This type of operation can promote the dehydrogenation reaction by providing for the removal of hydrogen between reactors and thereby increasing the conversion and selectivity of the dehydrogenation reaction of this invention. By using this two-pass process conversion was increased from 90.7% for the first pass to 98.7% after the second pass, as demonstrated by a comparison of the data from Example 53 in Table 9 to the overall conversion reported in Table 9.

From the above description, it is apparent that the objects of the present invention have been achieved. While only certain embodiments have been set forth, alternative embodiments and various modifications will be apparent from the above description to those skilled in the art. These alternatives are considered equivalents and are within the spirit and scope of the present invention.

Having described the invention, what is claimed is:

1. A method for preparing a dimethylnaphthalene, comprising: contacting a first feedstock comprising at least one dimethyltetralin in liquid form with a solid dehydrogenation catalyst in a reaction vessel at an elevated temperature and at a pressure that is sufficiently high to maintain the first feedstock substantially in the liquid phase, to thereby effect conversion of the aforesaid dimethyltetralin in an equilibrium dehydrogenation reaction to form hydrogen and a first liquid product comprising a dimethylnaphthalene formed from each aforesaid dimethyltetralin, and removing a substantial portion of the hydrogen being formed in the dehydrogenation reaction from the reaction vessel to thereby shift the aforesaid equilibrium toward the formation of the dimethylnaphthalene product.

2. The method of claim 1 wherein either (a) 1,5-, 1,6-, 2,5-, or 2,6-dimethyltetralin or a mixture thereof comprises at least 80 weight percent of the dimethyltetralin content of the first feedstock, and 1,5-, 1,6- or 2,6-dimethylnaphthalene or a mixture thereof comprises at least 80 weight percent of the methylnaphthalene content of the first liquid product, (b) 1,5-, 1,6-, 1,7-, 1,8-, 2,5-, 2,6-, 2,7-, or 2,8-dimethyltetralin or a mixture thereof comprises at leas. 80 weight percent of the dimethyltetralin content of the first feedstock and 1,5-, 1,6-, 1,7-, 1,8-, 2,6-, or 2,7-dimethylnaphthalene or a mixture thereof comprises at least 80 weight percent of the dimethylnaphthalene content of the first liquid product, (c) 1,7-, 1,8-, 2,7- or 2,8-dimethyltetralin or a mixture thereof comprises at least 80 weight percent of the dimethyltetralin content of the first feedstock and 1,7-, 1,8- or 2,7-dimethylnaphthalene or a mixture thereof comprises at least 80 weight percent of the dimethylnaphthalene content of the first liquid product, or (d) 1,3-, 1,4-, 2,3-, 5,7-, 5,8- or 6,7-dimethyltetralin or a mixture thereof comprises at least 80 weight percent of the dimethyltetralin content of the first feedstock and 1,3-, 1,4- or 2,3-dimethylnaphthalene or a mixture thereof comprises at least 80 weight percent of the dimethylnaphthalene content of the first liquid product.

3. The method of claim 2 wherein 1,5-, 1,6-, 2,5-, or 2,6-dimethyltetralin or a mixture thereof comprises at least 80 weight percent of the dimethyltetralin content of the first feedstock and 1,5-, 1,6- or 2,6-dimethylnaphthalene or a mixture thereof comprises at least 80 weight percent of the dimethylnaphthalene content in the first liquid product.

4. The method of claim 2 wherein 1,5-, 1,6-, 1,7-, 1,8-, 2,5-, 2,6-, 2,7-, or 2,8-dimethyltetralin or a mixture thereof comprises at least 80 weight percent of the dimethyltetralin content of the first feedstock and 1,5-, 1,6-, 1,7-, 1,8-, 2,6-, or 2,7-dimethylnaphthalene or a mixture thereof comprises at least 80 weight percent of the dimethylnaphthalene content of the first liquid product.

5. The method of claim 2 wherein 1,7-, 1,8-, 2,7or 2,8-dimethyltetralin or a mixture thereof comprises at least 80 weight percent of the dimethyltetralin content of the first feedstock, and 1,7-, 1,8- or 2,7-dimethylnaphthalene or a mixture thereof comprises at least 80 weight percent of the dimethylnaphthalene content of the first liquid product.

6. The method of claim 2 wherein 1,3-, 1,4-, 2,3-, 5,7-, 5,8- or 6,7-dimethyltetralin or a mixture thereof comprises at least 80 weight percent of the dimethyltetralin content of the first feedstock, and 1,3-, 1,4- or 2,3-dimethylnaphthalene or a mixture thereof comprises at least 80 weight percent of the dimethynaphthalene content of the first liquid product.

7. The method of claim 2 wherein the dehydrogenation is performed at a temperature in the range of from about 200° C. to about 500° C.

8. The method of claim 2 wherein the dehydrogenation is performed at a pressure in the range of from about 0.1 to about 30 atmospheres absolute.

9. The method of claim 2 wherein the dehydrogenation catalyst comprises a noble metal component supported on a substantially inert support material, with the noble metal component employed at a level of from about 0.5 to about 15 weight percent, calculated as the elemental noble metal and based on the weight of the dehydrogenation catalyst.

10. The method of claim 9 wherein the noble metal component comprises palladium.

11. The method of claim 9 wherein the dehydrogenation is performed continuously with a space velocity in the range of from about 0.1 to about 5000 parts of the feedstock per part of the noble metal component (calculated as the elemental noble metal) of the dehydrogenation catalyst by weight per hour.

12. The method of claim 9 wherein the dehydrogenation is performed on a batch basis with the dehydrogenation catalyst at a level in the range of from about 0.005 to about 1.0 percent of the noble metal component, calculated as the elemental noble metal, and based on the weight of the dimethyltetralin feedstock and the reaction time is from about 1 to about 50 hours.

13. The method of claim 2 wherein the second feedstock is dissolved in a solvent.

14. The method of claim 13 wherein the solvent is a paraffin or aromatic hydrocarbon which boils above about 270° C.

15. The method of claim 2 comprising the additional steps of: contacting the aforesaid first liquid product in liquid form with a solid isomerization catalyst comprising beta zeolite or an acidic ultrastable Y-crystalline zeolite having a silica-to-alumina molar ratio of from about 4 to about 10, and having pore windows provided by twelve-membered rings containing oxygen and a unit cell size of from about 24.2 to about 24.7 angstroms, and at an elevated temperature and at a pressure that is sufficiently high to maintain the isomerization feedstock substantially in the liquid phase wherein (1) when at least 80 weight percent of the dimethylnaphthalene content of the first liquid product comprises at least one of 1,5-, 1,6-, and 2,6-dimethylnaphthalene, at least 20 weight percent of the total of 1,5- and 1,6-dimethylnaphthalenes is isomerized to 2,6-dimethylnaphthalene, (2) when at least 80 weight percent of the dimethylnaphthalene content of the first liquid product comprises at least one of 1,5-, 1,6-, 1,7-, 1,8-, 2,6- and 2,7-dimethylnaphthalenes, at least 20 weight percent of the total of 1,5-, 1,6-, 1,7- and 1,8-dimethylnaphthalenes is isomerized to 2,6- and 2,7-dimethylnaphthalenes, (3) when at least 80 weight percent of the dimethylnaphthalene content of the first liquid product comprises at least one of 1,7-, 1,8- and 2,7-dimethylnaphthalene, at least 20 weight percent of the total of 1,7- and 1,8-dimethylnaphthalenes is isomerized to 2,7-dimethylnaphthalene, and (4) when at least 80 weight percent of the dimethylnaphthalene content of the first liquid product comprises at least one of 1,3-, 1,4- and 2,3-dimethylnaphthalenes, at least 20 weight percent of the total of 1,3- and 1,4-dimethylnaphthalenes is isomerized to 2,3-dimethylnaphthalene.

16. The method of claim 15 wherein at least 25 weight percent of the total of 1,5- and 1,6-dimethylnaphthalenes in the aforesaid first liquid product in (1) of claim 15 is isomerized to 2,6-dimethylnaphthalene.

17. The method of claim 15 wherein at least 25 weight percent of the total of 1,5-, 1,6-, 1,7- and 1,8-dimethylnaphthalenes in the aforesaid first liquid product in (2) of claim 15 is isomerized to 2,7-dimethylnaphthalene and 2,6-dimethylnaphthalene.

18. The method of claim 15 wherein at least 25 weight percent of the total of 1,7- and 1,8-dimethylnaphthalenes in the aforesaid first liquid product in (3) of claim 15 is isomerized to 2,7-dimethylnaphthalene.

19. The method of claim 15 wherein at least 25 weight percent of the total of 1,3- and 1,4-dimethylnaphthalenes in the aforesaid first liquid product in (4) of claim 15 is isomerized to 2,3-dimethylnaphthalene.

20. The method of claim 15 wherein the isomerization is performed at a temperature in the range of from about 200° C. to about 420° C.

21. The method of claim 15 wherein the isomerization is performed on a batch basis.

22. The method of claim 15 wherein the isomerization catalyst employed comprises beta zeolite.

23. The method of claim 22 wherein the isomerization catalyst comprises a hydrogenation component comprising a Group VIII metal.

24. The method of claim 23 wherein the Group VIII metal is palladium, platinum or nickel.

25. The method of claim 21 wherein the isomerization catalyst employed is free of a support material.

26. The method of claim 21 wherein the isomerization catalyst is supported on an inorganic support material.

27. The method of claim 26 wherein the support material comprises silica, alumina, silica-alumina, or bentonite, or magnesia, or a mixture thereof.

28. The method of claim 15 wherein the isomerization is performed at a pressure in the range of from about 0.1 to about 20 atmospheres absolute.

29. The method of claim 15 wherein the isomerization is performed on a continuous basis with a space velocity of, or on a batch basis with an effective space velocity of, from about 0.1 to about 20 parts of feedstock per part of the zeolite component of the isomerization catalyst by weight per hour.

30. The method of claim 1 wherein the dehydrogenation catalyst comprises a mixture of platinum and rhenium supported on an alumina support.

31. The method of claim 30 wherein the platinum and rhenium are each present in an amount of about 0.01 to about 10.0 weight percent calculated based on the weight of the catalyst and wherein the alumina support comprises gamma alumina.

32. The method of claim 1 wherein the dehydrogenation reaction is performed continuously using at least two series arranged fixed bed reactors and wherein hydrogen is removed from the liquid product between the fixed bed reactors.

33. The method of claim 1 wherein said reaction vessel is a fixed bed reactor.

* * * * *

UNITED STATES PATENT OFFICE
CERTIFICATE OF CORRECTION

Patent No.  5,118,892              Dated   June 2, 1992

Inventor(s)  SIKKENGA et al.

It is certified that error appears in the above-identified patent and that said Letters Patent is hereby corrected as shown below:

| Column | Line |  |
|---|---|---|
| 13 | Line 65 | "ion-exchanged Some" should read --ion-exchanged. Some-- |
| 14 | Line 48 | "6 hours" should read --6 hours.-- |
| 21 | Line 52 | "of the methylnaphthalene content" should read --of the dimethylnaphthalene content-- |
| 21 | Line 55 | "at leas. 80 weight percent" should read --at least 80 weight percent-- |

Signed and Sealed this

Thirty-first Day of August, 1993

Attest:

BRUCE LEHMAN

Attesting Officer        Commissioner of Patents and Trademarks